(12) United States Patent
Evans

(10) Patent No.: US 7,241,315 B2
(45) Date of Patent: Jul. 10, 2007

(54) FEMORAL HEAD RESURFACING APPARATUS AND METHODS

(76) Inventor: Robert Evans, P.O. Box 243, Chautauqua, NY (US) 14722

( * ) Notice: Subject to any disclaimer, the term of this patent is extended or adjusted under 35 U.S.C. 154(b) by 189 days.

(21) Appl. No.: 10/937,047

(22) Filed: Sep. 9, 2004

(65) Prior Publication Data
US 2005/0033447 A1 Feb. 10, 2005

Related U.S. Application Data

(63) Continuation-in-part of application No. 10/200,239, filed on Jul. 22, 2002, now abandoned.

(60) Provisional application No. 60/307,244, filed on Jul. 23, 2001.

(51) Int. Cl.
  *A61F 2/36* (2006.01)
  *A61F 2/32* (2006.01)
(52) U.S. Cl. .................................. 623/23.12; 623/22.21
(58) Field of Classification Search .............. 623/23.12, 623/23.14, 23.11, 22.11, 23.13, 22.23
See application file for complete search history.

(56) References Cited

U.S. PATENT DOCUMENTS

| 4,035,848 | A | | 7/1977 | Wagner | |
|---|---|---|---|---|---|
| 5,133,764 | A | * | 7/1992 | Pappas et al. | 623/23.14 |
| 5,725,593 | A | * | 3/1998 | Caracciolo | 623/22.23 |
| 5,800,557 | A | * | 9/1998 | Elhami | 623/23.12 |
| 6,156,069 | A | | 12/2000 | Amstutz | |
| 6,746,452 | B2 | * | 6/2004 | Tuke et al. | 606/91 |
| 2002/0049501 | A1 | | 4/2002 | Storer et al. | |

* cited by examiner

*Primary Examiner*—Cris Rodriguez
*Assistant Examiner*—Candice C. Stokes
(74) *Attorney, Agent, or Firm*—Lathrop & Gage LC

(57) ABSTRACT

A femoral head resurfacing apparatus includes a cap of hemispherical shape and stabilization structure (e.g., one or more non-shear fixation bars) that inserts into slots cut into the femoral head, so that the cap remains substantially immovable other than due northerly. A method of resurfacing the femoral head of a hip joint includes removing longitudinal slots or holes of bone in the femoral head, and attaching a hemispherical cap to the head, the cap having non-shear fixation bars or other stabilizing structure for mating engagement with the slots or holes.

18 Claims, 22 Drawing Sheets

FEMORAL HEAD RESURFACING APPARATUS AND METHODS

RELATED APPLICATIONS

This application is a continuation-in-part of U.S. patent application Ser. No. 10/200,239 filed Jul. 22, 2002, now abandoned which claims priority to U.S. Provisional patent Application Ser. No. 60/307,244, entitled "Total Hip Joint Replacement Prosthesis" filed Jul. 23, 2001, each of which is incorporated herein by reference.

BACKGROUND OF THE INVENTION

Various partial or complete replacements of the hip joint have been proposed and used since the early 1900's. Most of the procedures or methods involved material problems that led to joint loosening and consequential failure.

One widely used total hip replacement removes the femoral head and inserts a stem into the upper end of the femur, where it is fixed either by cement or by bone growth into a porous coating. A small metal ball, replacing the patient's femoral ball, is affixed to the stem. This technique requires massive bone removal and results in extreme loading of force in a leveraging action from the top of the femoral ball to a lower part of the stem. Over a few years, force applied by vigorous and mostly younger patients can cause the stem to loosen, resulting in failure, pain and need for extensive and expensive revisions.

When a patient has enough bone stock, a resurfacing approach may be used. In one example, the femoral head is resurfaced with a singular fixation approach that uses either cementing or bone ingrowth into a porous surface or surfacing material. However, with the singular fixation approach, the probability of failure remains high because there is no mechanism to back up, reinforce and absorb large downward forces and subsequent reactionary forces applied through vigorous activity.

Accordingly, after a hip joint replacement utilizing prior art techniques, slight movements (up to about 0.08 mm per year) of a replacement shell relative to a femoral ball may occur and are deemed "acceptable migration." Single point fixation methods typically mitigate this problem with respect to only one degree of freedom in movement; for example, a centering post can stop a cap or shell from migrating longitudinally, but does not prevent it from migrating equatorially. The polar north direction is not a problem, in that anatomically most force applied to a femoral head is driving the shell on, versus pulling it off. Cement is capable of preventing loosening in the polar north direction. However, the equatorial direction receives a larger shear stress. Elasticity of typical cements allows "acceptable migration" due to the application of force, but when a cement's coefficient of elasticity is reached, the cement will fail with significant loosening, requiring a revision. Other factors that can contribute to cement failure are:

1. Variance in quality of manufactured cement—Quality control
2. Variance in bone composition from one individual to another, which could mean a difference in adhesion
3. Variance in operation technique.
4. Too much or too little cement applied.
5. Foreign material getting into the cement.
6. Different levels of patient activity may exert significantly higher amounts of force on the shell, causing varying degrees of migration.

SUMMARY OF INVENTION

Multiple embodiments of femoral resurfacing apparatus (including a femoral cap or shell, hereinafter "cap") and fixation methods are disclosed that may require less bone removal than prior art caps and methods; they may also maintain the naturally occurring femoral head shape, to accept and evenly distribute applied and reactionary forces to the femur and lessen the potential for shearing and loosening of the cap. Methods of fixation may employ different approaches to absorb a portion of the applied and reactionary shearing forces generated by highly active patients, thus reducing the possibility of loosening (a principal cause of hip joint replacement failure).

In one method, mechanical fixation uses internal metal non-shear bars (e.g., three non-shear bars) that are 5–8 mm wide and about 4 mm deep; slots cut into the femoral ball accommodate the non-shear bars. The non-shear bars are an integral part of a hemispherical femoral cap, and reinforce and strengthen the cap to withstand shear forces many times those which are generated by vigorous activity. Therefore, this method of fixation prevents lateral and longitudinal rotation of the cap, while utilizing only two components that can shear or loosen (e.g., the cap and the bone). Accordingly, the cap can separate from the femoral ball in only one direction: due northerly, that is, straight off the femoral ball without rotation. This direction of separation may be mechanically prevented by metal spring loaded absorption fixators (SLAFs) that screw into the ends of the non-shear bars at their hemispherical ends. The SLAFs extend downward, for example 10–15 mm, whereupon they are separated from the side of the femoral ball by approximately 3 mm. Each spring loaded absorption fixator (SLAF) may be screwed into the femoral ball, pulling the tab against the side of the lower femoral ball. A load for each SLAF may be selected from a range of 30# to 130# to (1) provide a southerly retention force equal to, for example, one third of the patient's body weight on the cap, and (2) absorb a portion of the applied and reactionary forces received by the femoral ball similar to normal bone flexation. Additionally, the screws may be prevented from backing out by seating them deep enough within the SLAF so that a small flat metal anti-back out tab can be inserted into a slot running parallel to the head surface of each screw. Once this anti-back out tab is inserted into the slot, it may drop down into a position lower than the slot itself, so that it can not come out without the use of special removal tools. The anti-back out tab sits on top of the head of the screw to prevent back out of the screw. In addition, threads of the bone screws may be notched so that, once in place, bone will grow into the notches, providing a back up anti-back out screw fixation method. The lower or southerly ends of the SLAFs may also be coated with hydroxyapatite porocast, or other materials, to create fixation via bone ingrowth.

Another method of preventing a separation or loosening of a cap in a northerly or straight off non-rotational direction is by bone-to-bone growth through gear tooth shaped teeth cast into the bottom surface of the non-shear bars starting northerly about 8 mm from the hemispherical end of each bar and running about 15 mm down each non-shear bar. Each tooth is about 2 mm deep and 2 mm wide. A coating with hydroxyapatite porocast reduces the depth and width to about 1 mm, providing for substantial purchase through bone growth into the teeth from three directions.

A third method of fixation may employ a coating of the interior of the shell with hydroxyapatite porocast, or similar bone ingrowth fixation material, to prevent separation or loosening of the cap in all directions.

In one non-limiting example of a total hip joint replacement operation, access to the hip joint is achieved through separation of the trochanter, which protrudes from the upper portion of the upper leg bone (the femur) from the rest of the leg, together with dislocation of the hip joint itself. After dislocation, the femoral ball is reamed down to accommodate a hemispherical, hollow cap that has approximately the same outside diameter as the patient's (pre-ream) femoral ball. Upon completion of the reaming process, the femoral ball remains substantially hemispherical, with its diameter and surface reduced by 4 mm to 5 mm in order to accommodate the metal alloy femoral cap. Additionally, slots are cut longitudinally an equal distance apart in the femoral ball, to accommodate the non-shear bars within the cap that run perpendicular to the equatorial edge or lip of the cap north/south from its polar orientation a distance of 25 mm to 30 mm. With the non-shear bars, the cap cannot separate from the femoral ball through rotation, laterally or longitudinally. The cap is also mechanically fixed by SLAFs screwed to the internal longitudinal cap's non-shear bars, and subsequently to the femoral ball, by full thread cancellous screws about 4 mm long; thus securing the cap so that it can not separate from the femoral ball by traveling in a non-rotational direction due north. Additionally, the underside of the lower end of the SLAFs may be coated with hydroxyapatite porocast to provide a second fixation method for the SLAFs, through bone growth into a hydroxyapatite porocast surface. Additionally, the internal longitudinal non-shear bars' lower surfaces, which face the bottom of the slots, may include gear teeth that allow bone to grow more substantially into the teeth, providing a third method of fixing the cap to the femoral ball, so that the cap can not move or separate from the femoral ball in a straight cephalad northerly direction. Further fixation may be achieved by coating the inside surface of the cap between the non-shear bars with hydroxyapatite porocast, or similar materials, to fixate the cap to the femoral head by bone ingrowth.

In one embodiment, a femoral head resurfacing apparatus includes (a) a cap with a substantially hemispherical shape of substantially uniform thickness, and (b) one or more non-shear fixation bars that insert into respective longitudinal slots cut into the femoral head, so that the cap remains substantially immovable other than due northerly. The non-shear fixation bars may include a plurality of gear shaped teeth to encourage bone ingrowth between the teeth.

In another embodiment, a femoral head resurfacing apparatus includes (a) a chromium-cobalt-molybdenum alloy cap having a substantially hemispherical shape of substantially uniform thickness, and (b) a plurality of non-shear fixation bars for insertion into respective longitudinal slots cut into the femoral head, so that the cap remains substantially immovable other than due northerly. The cap may interface with a metal cup socket maintaining a clearance tolerance of approximately 0.01 mm.

In another embodiment, a femoral head resurfacing apparatus includes (a) a cap having a substantially hemispherical shape of substantially uniform thickness, and (b) a plurality of non-shear fixation bars for insertion into respective longitudinal slots cut into the femoral head, so that the cap remains substantially immovable other than due northerly. The cap may be fixed by a plurality of metal spring loaded absorption fixators, each fixator being screwed into the cap and femoral head, to prevent loosening of the cap.

In another embodiment, a method of resurfacing the femoral head of a hip joint includes removing longitudinal slots of bone in the femoral head, and attaching a hemispherical cap to the head. The cap has non-shear fixation bars that engage with the slots.

In another embodiment, a hollow femoral head resurfacing cap includes non-shear bars for mating engagement with longitudinal slots within a femoral head, and spring-loaded absorption fixators for attaching the cap to the head.

In another embodiment, a method for capping a femoral head with a shell includes inserting a centering device in a centering hole of the femoral head, drilling holes about the centering hole, and inserting fin-like dowels, which are a part of the centering hole post, into the holes to prevent migration of the shell. The three hole diameters may vary in size from about 3 mm to 12 mm; their depth may be about 6 mm.

In another embodiment, a femoral head resurfacing apparatus includes (a) a cap of hemispherical shape, (b) a center post for insertion into a center hole in the femoral head; and (c) stabilization structure for insertion into one or more corresponding holes in the femoral head, so that the cap remains substantially immovable other than due northerly

DETAILED DESCRIPTION OF THE DRAWINGS

Figure 1:
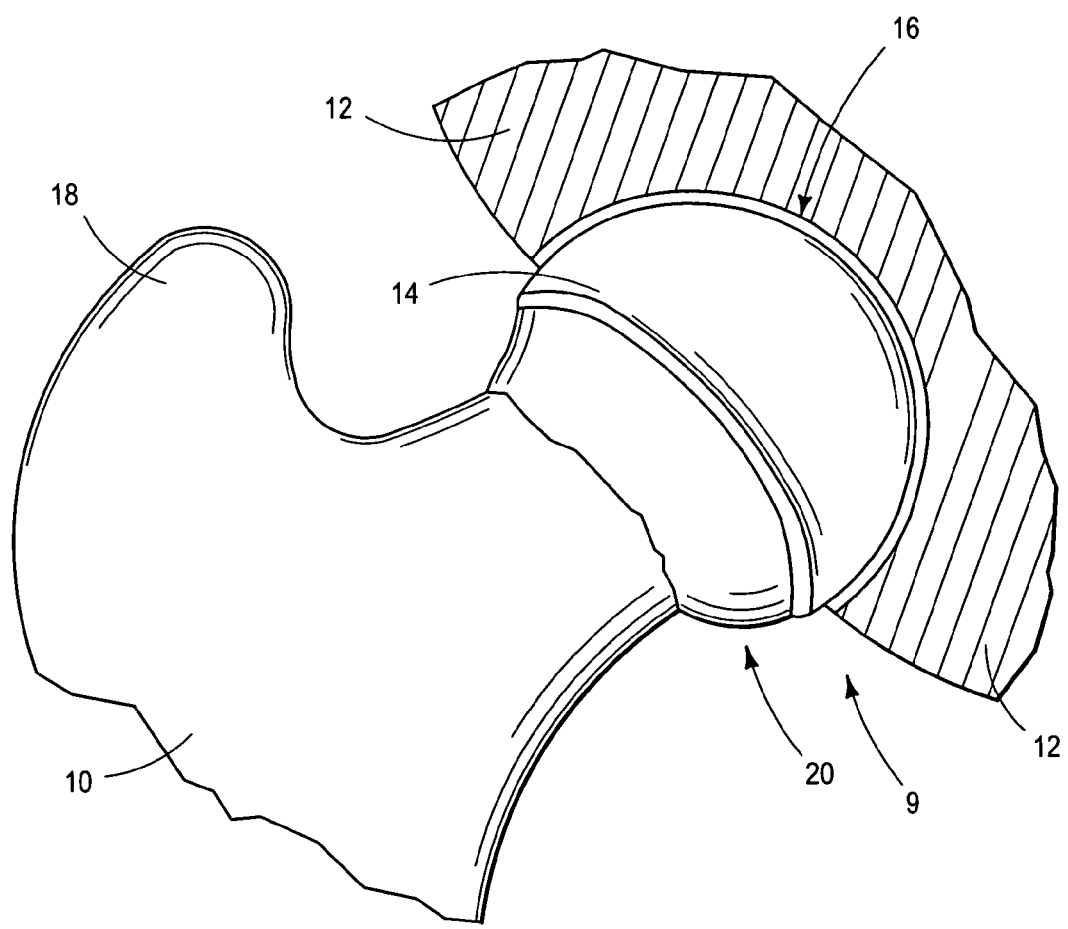
FIG. 1 shows an upper end of a femur, a pelvis with a metal actabular cup, and a femoral head resurfacing apparatus, in accord with one embodiment.

FIG. 1 shows an upper end of a large upper leg bone, namely a femur 10, a pelvis 12 with a metal actabular cup 16, and a femoral head resurfacing apparatus 9 that includes a femoral head resurfacing cap 14, in accord with one embodiment. A trochanter 18 is a large protuberance at the upper end of femur 10. Many major muscles which secure a femoral head 20 into a socket of the pelvis 12 attach to trochanter 18; accordingly, separation of trochanter 18 from femur 10 permits a dislocation of the hip joint fairly easily, giving good access to diseased areas of an arthritic or otherwise diseased hip joint.

Figure 2:
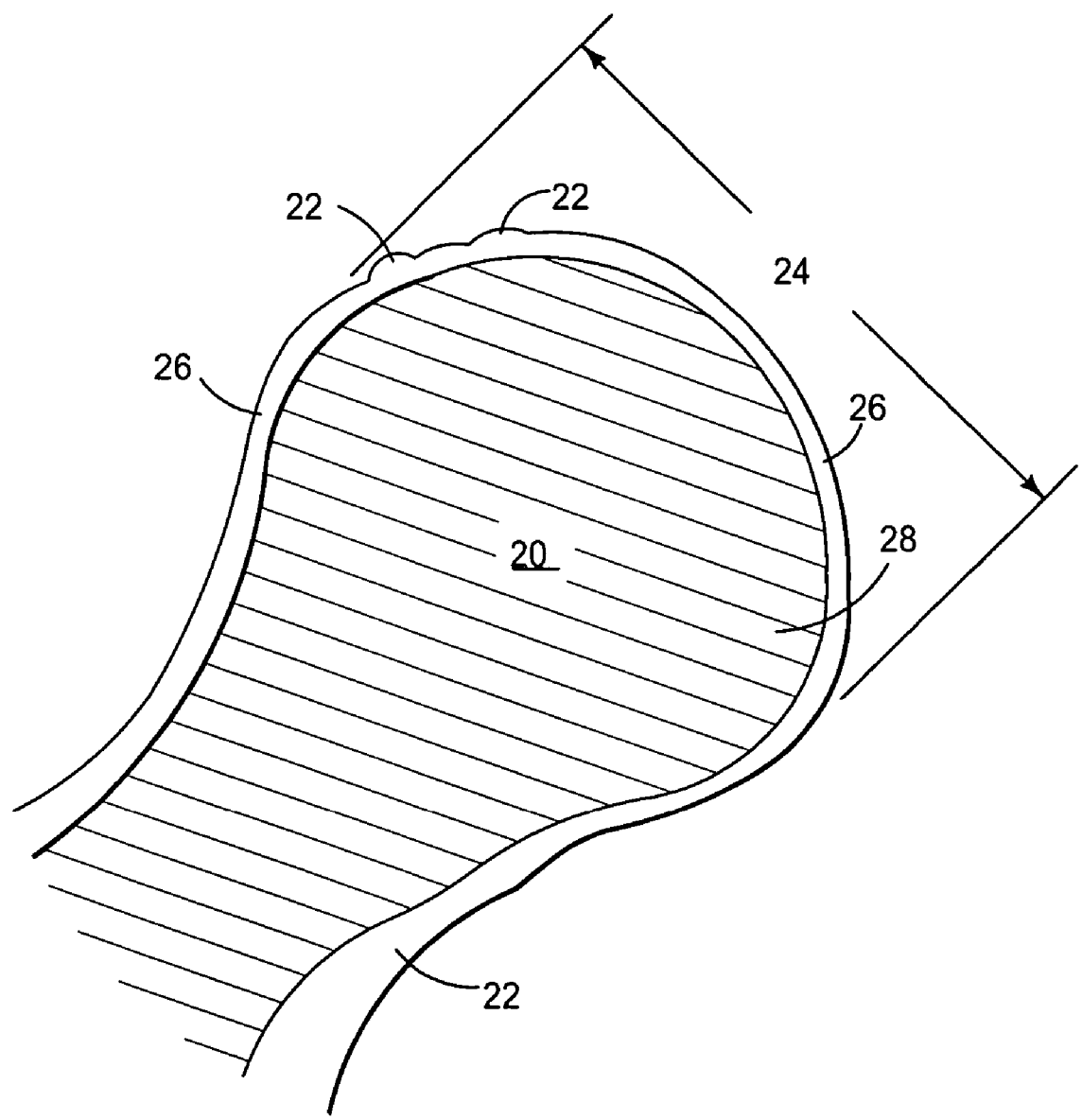
FIG. 2 is a cross-sectional view of a femoral head with arthritic calcifications.
Figure 3:
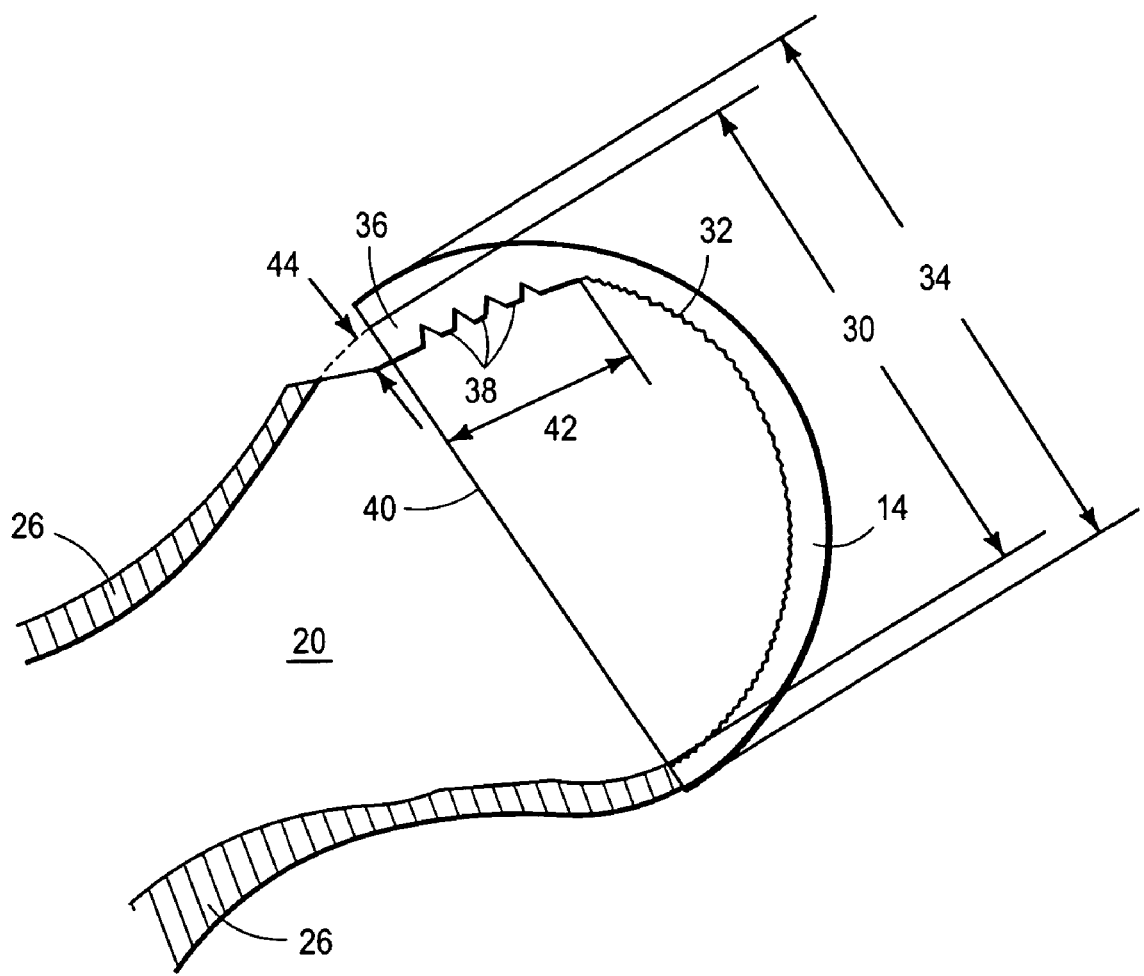
FIG. 3 is a cross-sectional view of a femoral head, after down size reaming, and a femoral head resurfacing cap in accord with one embodiment.

FIG. 2 is a cross-sectional view of a femoral head 20 with arthritic calcifications 22 and an outside diameter (O.D.) 24, prior to reaming off arthritic calcifications 22 and reducing the femoral head 20 to accept femoral head resurfacing cap 14, as shown in FIG. 3. Harder outer bone structure 26 of femoral head 20 is shown without cross hatching, and a strong calcificous inner portion 28 of femoral head 20 is shown with cross hatching.

FIG. 3 is a cross-sectional view of a femoral head 20, after down size reaming, and a femoral head resurfacing cap 14 in accord with one embodiment. Reaming reduces O.D. 24 by about 6 mm to form a modified O.D. 30, without changing the normal shape of femoral head 20. An inner surface of cap 14 may be coated with very small protuberances and indentations 32, such as a surface formed with a hydroxyapatite porocast process (to accept bone ingrowth), fixing cap 14 to femoral head 20. Cap 14 has an outside diameter 34 that is equal or close to the original size 24 of femoral head 20 (prior to reaming). Hard outer bone structure 26 is mostly removed from the top and sides of femoral head 20 during the reaming and shaping process, as shown in FIG. 3. Additionally, FIG. 3 shows one of three non-shear fixation bars 36 with gear shaped teeth 38 having a depth of about 2 mm and gaps between teeth of about 2 mm. Non-shear fixation bars 36 run within cap 14 from an equatorial plane or edge 40 northward by a distance 42 of about 18 mm, depending on the size of the cap 14 used. Each non-shear fixation bar 36 extends radially inward from an inner surface of the cap 36 by a distance 44 of about 4 mm, and is 5 mm to 8 mm in width (see FIG. 7).

Figure 4:
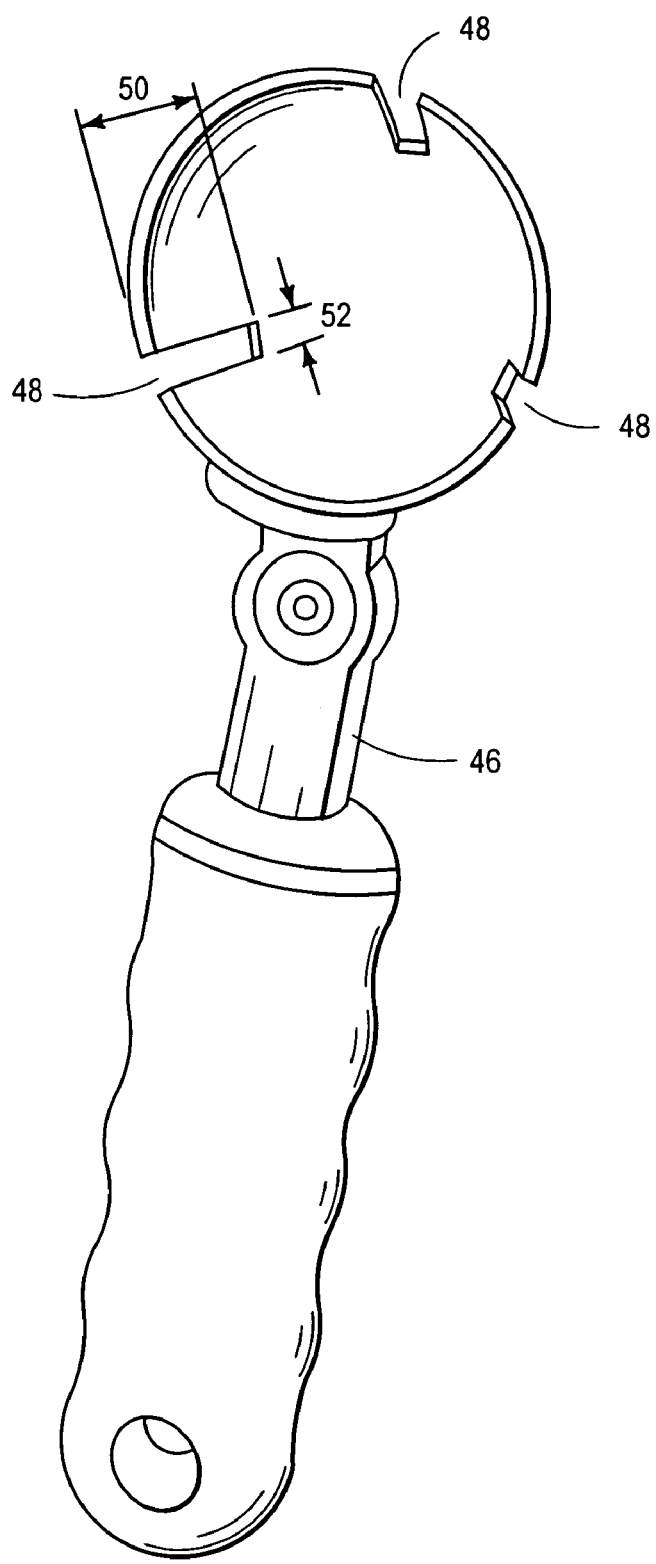
FIG. 4 is an internal view of a template device.

FIG. 4 is an internal view of a template device 46 having an inside diameter slightly larger than the reamed femoral ball outside diameter 30, FIG. 3. Once femoral head 20 has been reamed and downsized, template 46 may be placed over femoral head 20. Slots 48 in template device 46 are traced and marked on femoral head 20 at the locations at which the surgeon desires to cut slots for non-shear fixation bars 36 shown in FIGS. 3, 7 and 8. In one embodiment, slots 48 have a length 50 of 15 mm to 18 mm, and a width 52 of about 9 mm.

Figure 5:
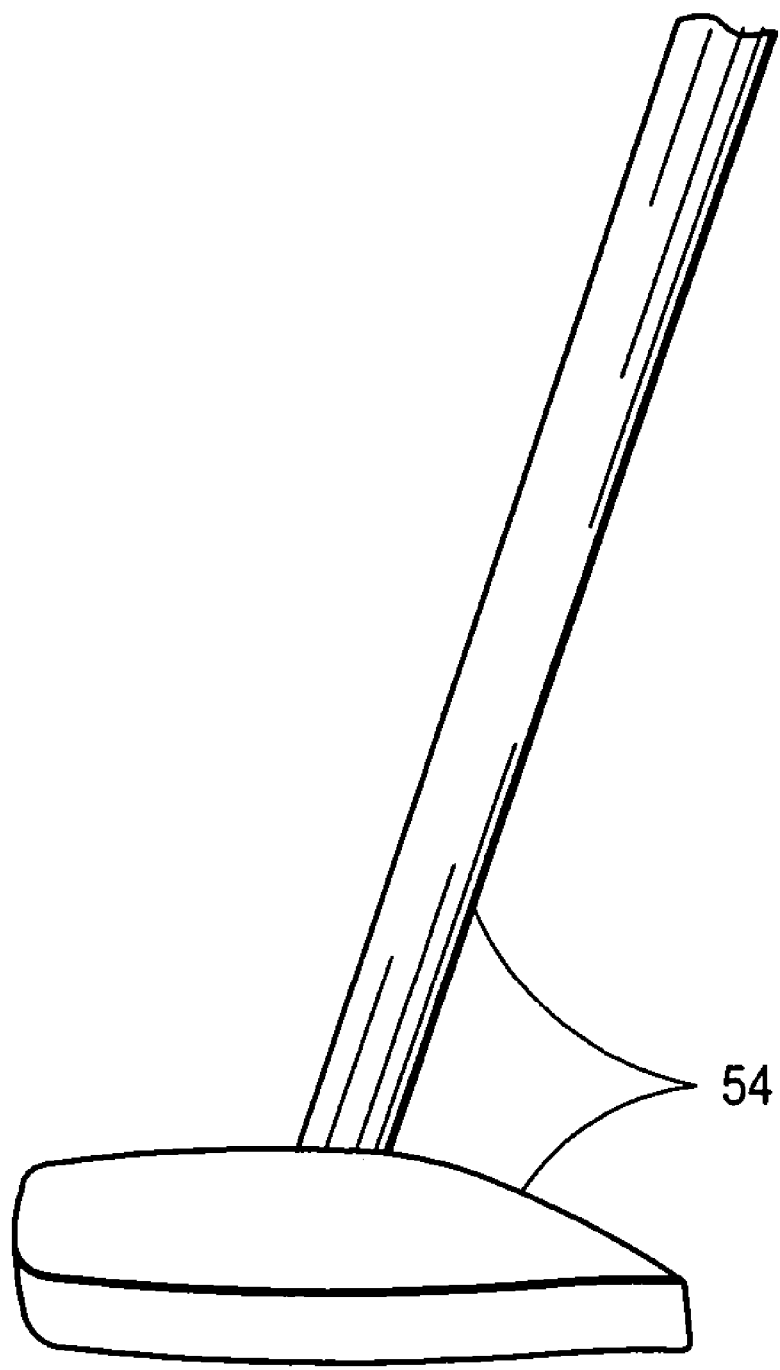
FIG. 5 is a side/bottom view of a depth gauge device.

FIG. 5 is a side/bottom view of a depth gauge device 54 that a surgeon may use to determine a correct depth to cut the traces of slots 48 on femoral head 20, so that the femoral head may receive the three non-shear fixation bars 36 located on the inner surface of the femoral cap 14.

Figure 6:
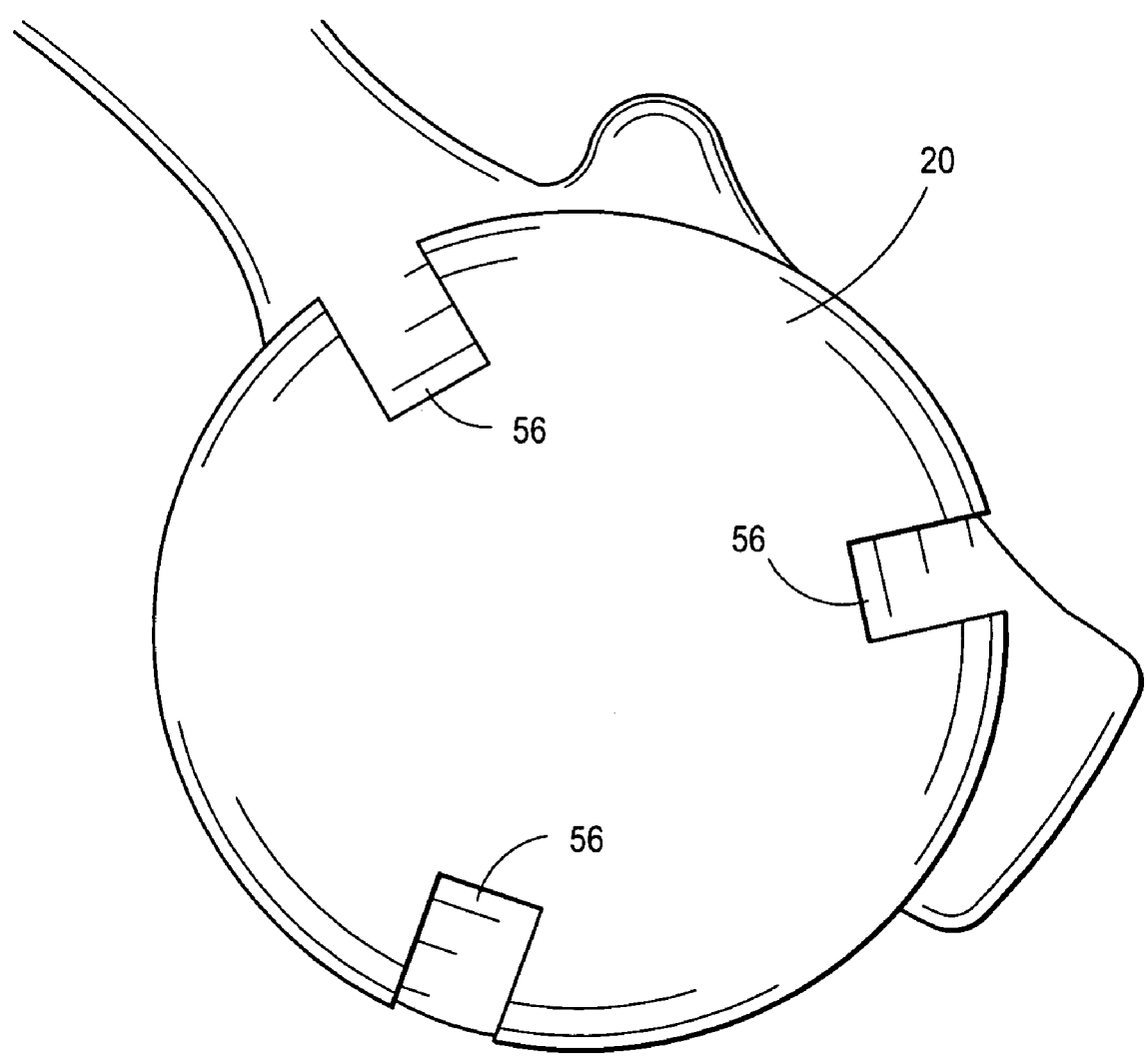
FIG. 6 shows a femoral head with three slots.
Figure 7:
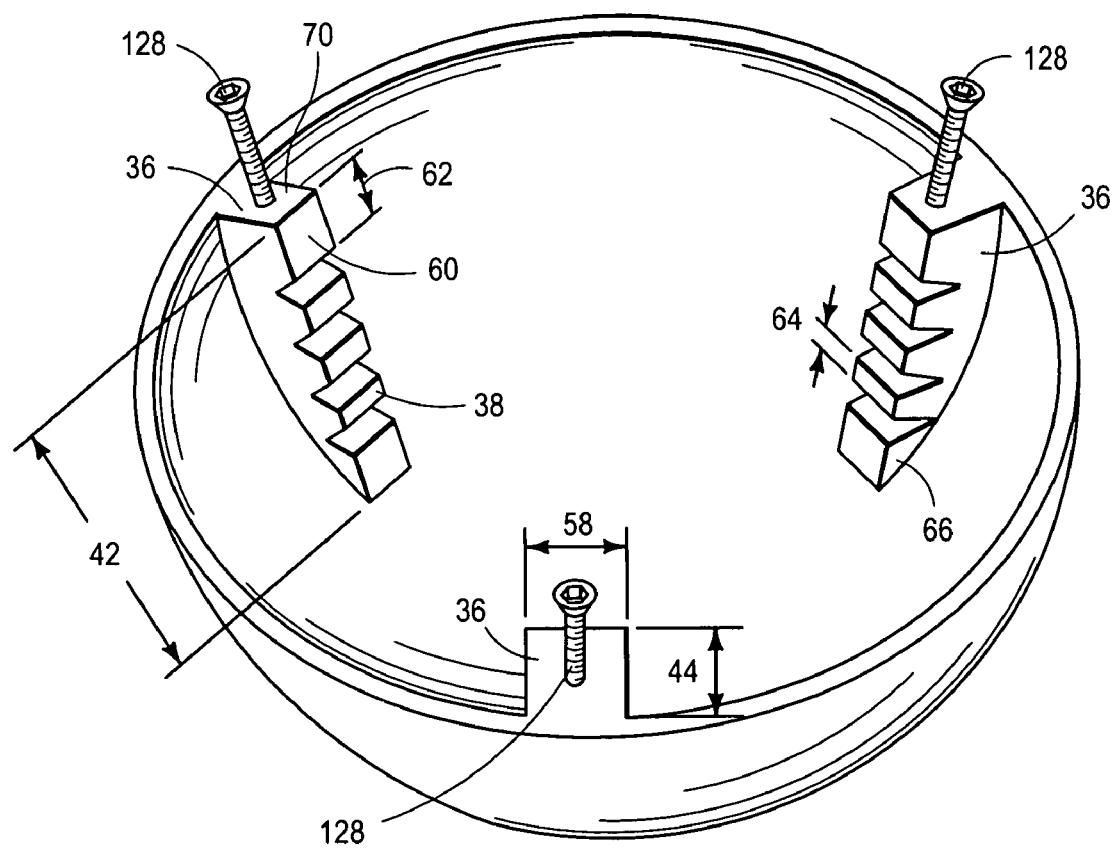
FIG. 7 is an internal view of a femoral head resurfacing cap showing three non-shear fixation bars, in accord with one embodiment.
Figure 8:
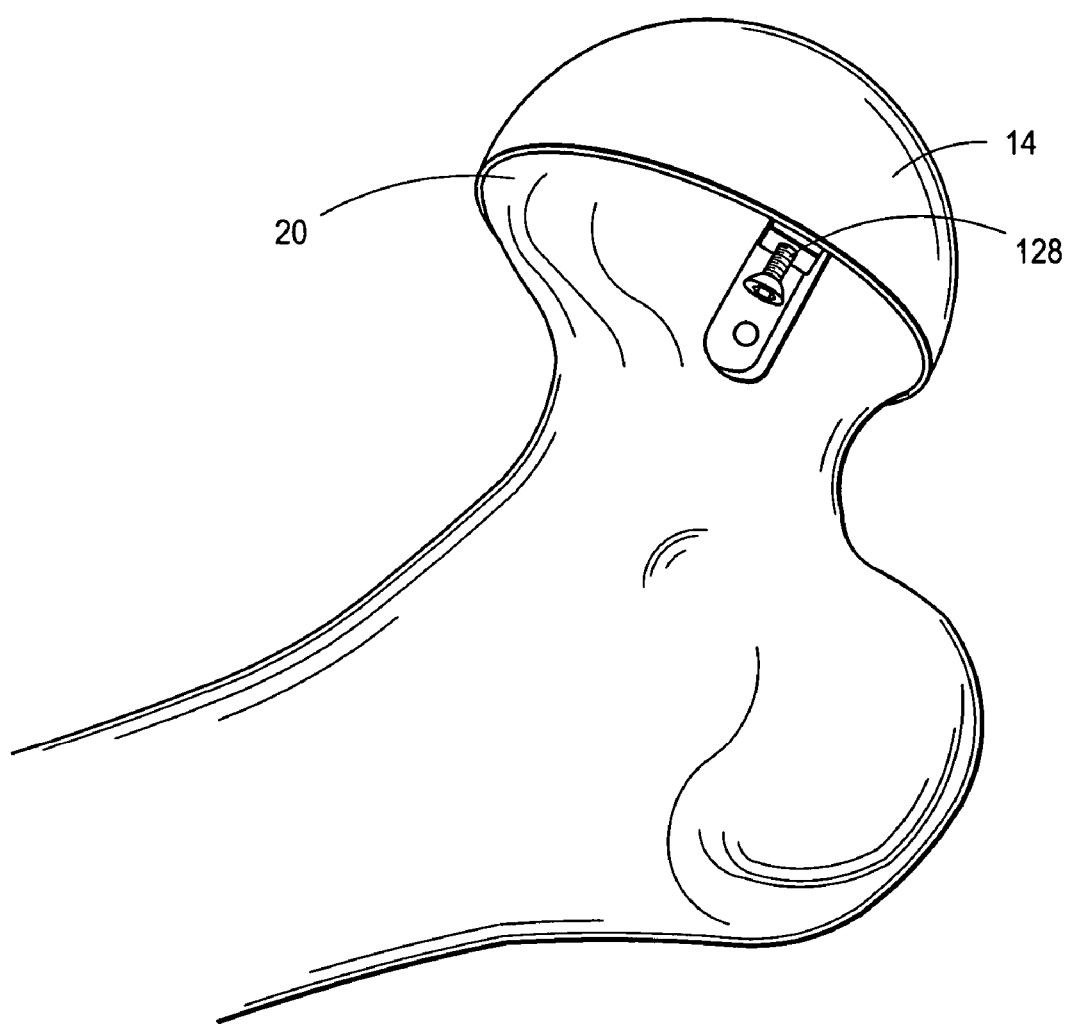
FIG. 8 shows the femoral head resurfacing cap of FIG. 7 in place, capping a femoral head.

FIG. 6 shows a femoral head 20 with three slots 56 cut in positions determined by a surgeon using template device 46, FIG. 4, to the depth indicated by depth gauge device 54, to accept the three non-shear bars 36 located on the inner surface of the cap 14 as shown in FIGS. 3, 7 and 8.

FIG. 7 is an internal view of a femoral head resurfacing cap 14 showing three non-shear fixation bars 36, in accord with one embodiment. Each non-shear fixation bar 36 has a depth 44 of about 4 mm, a width 58 of, for example, 5 mm to 8 mm, and a length 42 of about 18 mm. Each non-shear fixation bar 36 has, for example, three teeth 38 in an inner surface 60 of each bar, starting at a distance 62 of about 5 mm from a front equatorial end 70 of each non-shear fixation bar 36; each tooth 38 has a flat top width 64 of about 1 mm and an interior tooth depth 66 of about 2 mm. Gaps between the tops of adjacent teeth 38 are about 2 mm, and an interior angle or slope of each tooth 38 is, for example, 45 degrees. Teeth 38 may be coated with hydroxyapatite porocast, for bone ingrowth fixation, reducing the width and depth of each tooth by about 1 mm and increasing the depth of the non-shear fixation bars 36 by about 1 mm, for a total depth of about 5 mm. In addition, the sides of each non-shear fixation bar 36 may also be coated with hydroxyapatite porocast for additional bone ingrowth fixation, increasing the width of each non-shear fixation bar by the thickness of the coating (approximately 1 mm) for a total width ranging from 6 mm to 9 mm. The equatorial end 70 of each non-shear fixation bar 36 may be tapped to receive a machine screw 128, which may for example accept an Allen wrench. The thread and material design of machine screw 128 may be specified to withstand a shear force of about 1000 pounds.

FIG. 8 shows femoral head resurfacing cap 14 on femoral head 20.

Figure 9:
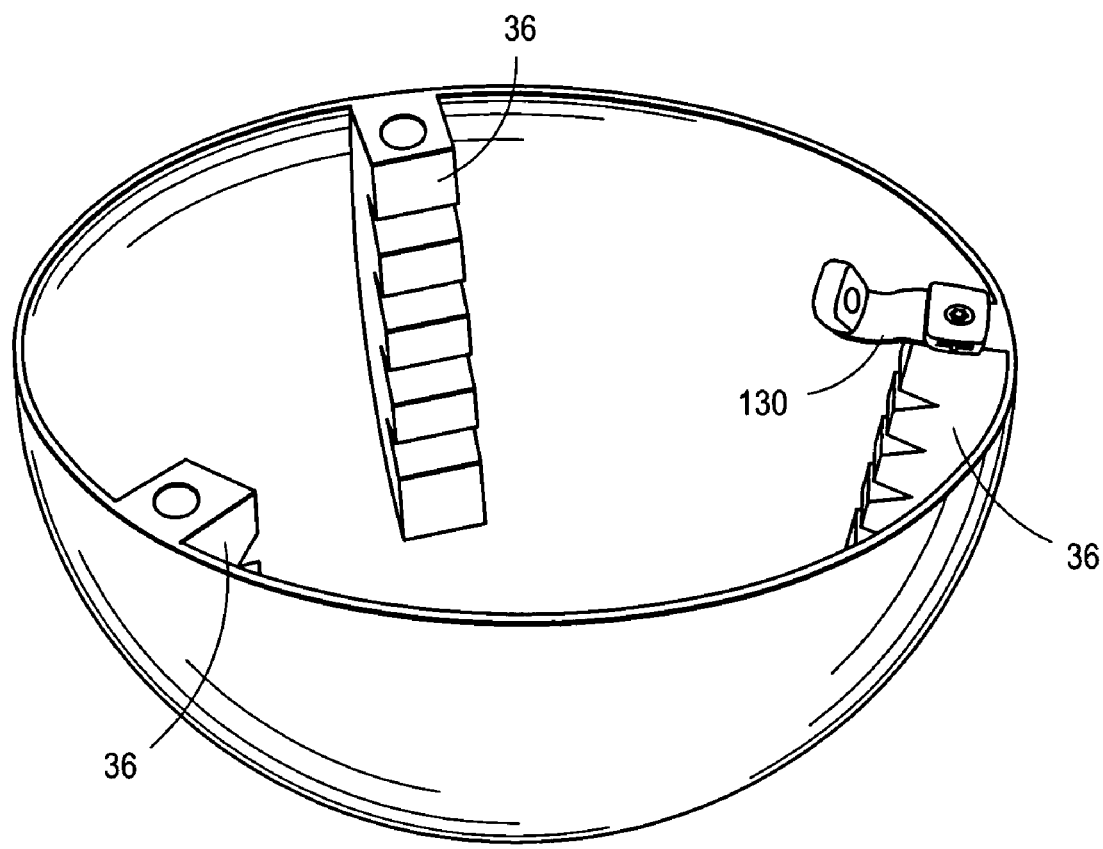
FIG. 9 shows a spring-loaded absorption fixator (SLAF) screwed into an equatorial end of a non-shear fixation bar, in accord with one embodiment.

FIG. 9 shows a spring loaded absorption fixator (SLAF) 130 screwed into equatorial end 70 (hidden in this view) of a non-shear fixation bar 36, in accord with one embodiment.

Figure 10:
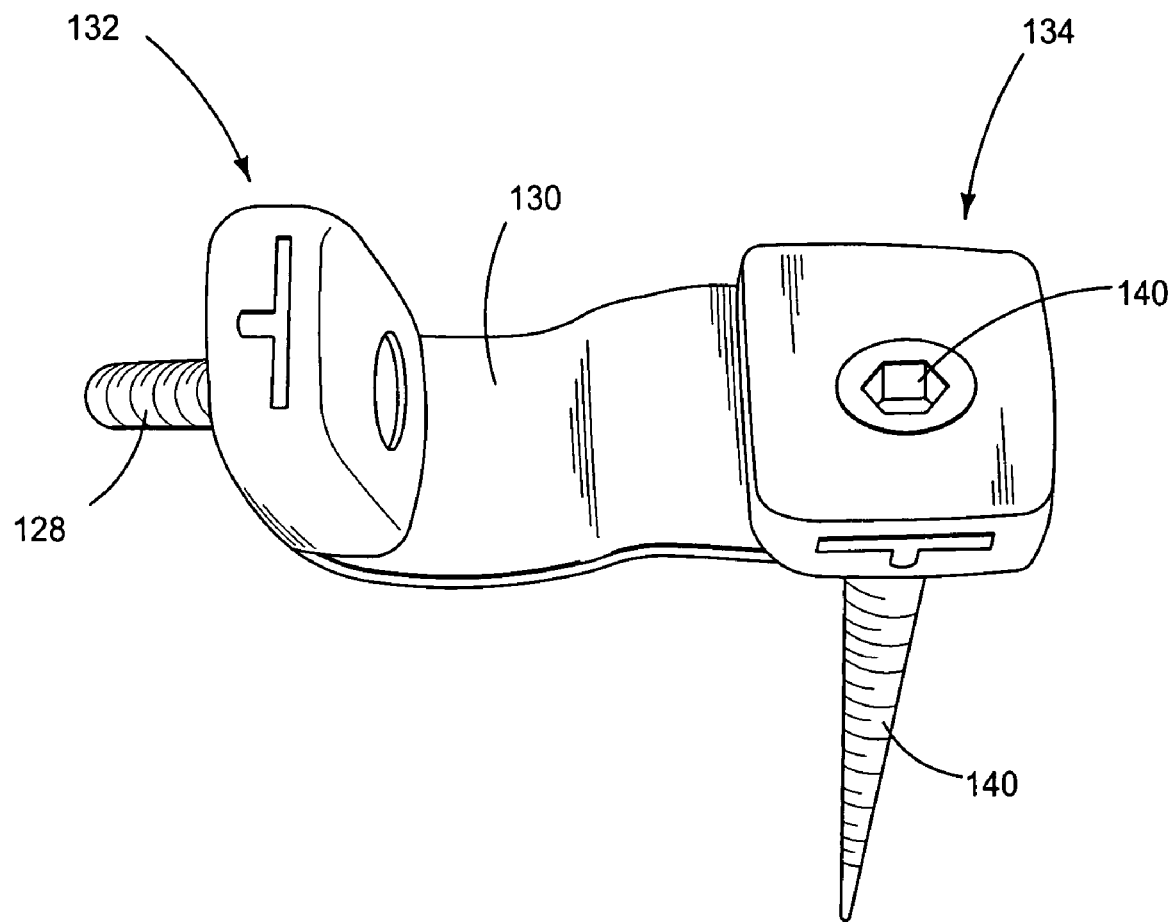
FIG. 10 shows further details of the SLAF of FIG. 9.
Figure 11:
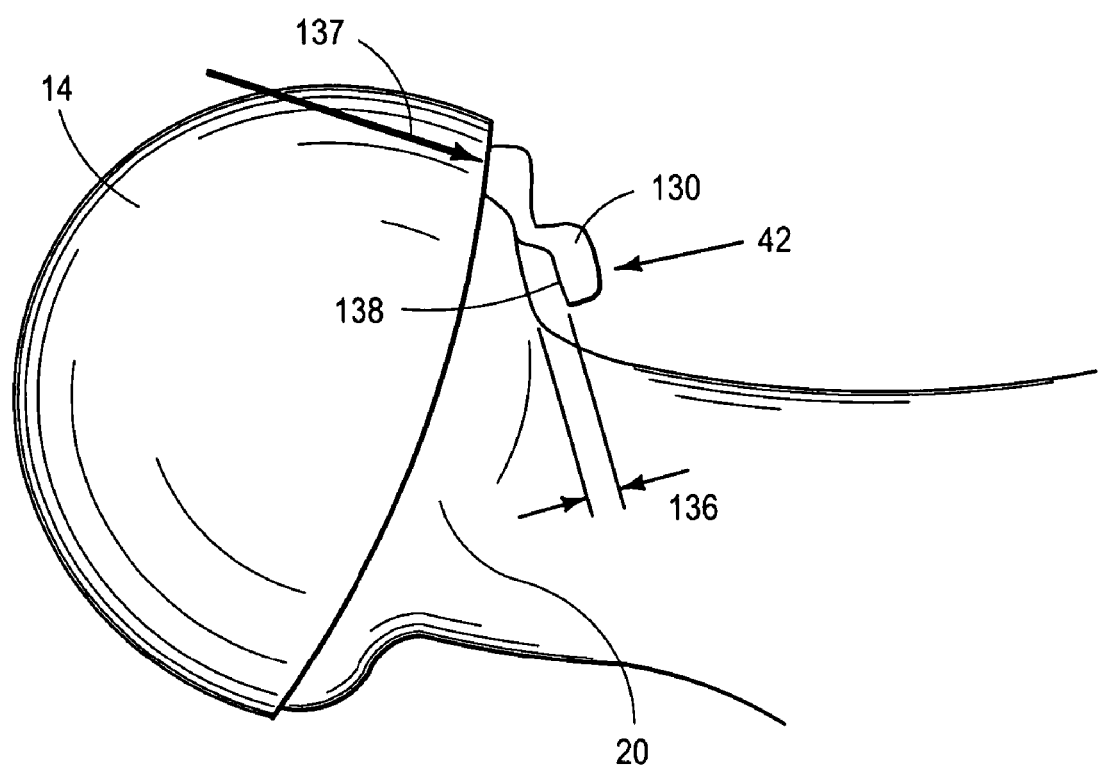
FIG. 11 shows the SLAF of FIG. 9 prior to being screwed onto a femoral head.

FIG. 10 shows, in further detail, SLAF 130 with a northerly end 132 and a southerly end 134. A machine screw 128 attaches a northerly end 132 of each SLAF 130 to an equatorial end 70 of non-shear bar 36, as shown in FIGS. 8 and 11. A bone screw 140 that attaches SLAF 130 to a femur 10 is also shown.

FIG. 11 shows one SLAF 130 prior to being screwed onto femoral head 20. Each SLAF 130 incorporates a bend of about 40 degrees, so that after being screwed into the cap 14, the opposite end is a distance 136 of about 3–4 mm off of femoral head 20. After bone screw 140 screws southerly end 134 onto femoral head 20, compression of SLAF 130 exerts a force 137 in a southerly direction on cap 14. Force 137 may be from one third to the total weight of the patient, depending on a stiffness of SLAF 130, which is selected by the surgeon. The stiffness of each SLAF 130 maybe selected from a range of 30 lbs. to 120 lbs. in 10 lb. increments, in order to provide a total southerly caudal retention force 137 on cap 14, and also to absorb a portion of the applied and reactionary forces received by the femoral head, similar to the flexation of the bone itself. SLAFs 130 may thus provide a continuous hold down or fixation force to the cap 14, while flexing like femur 10 to absorb applied downward and reverse reactionary forces, to reduce likelihood of shearing or breaking. Additionally, a southerly underside area 138 of SLAF 130 may be coated with hydroxyapatite porocast for additional bone ingrowth fixation.

Figure 12:
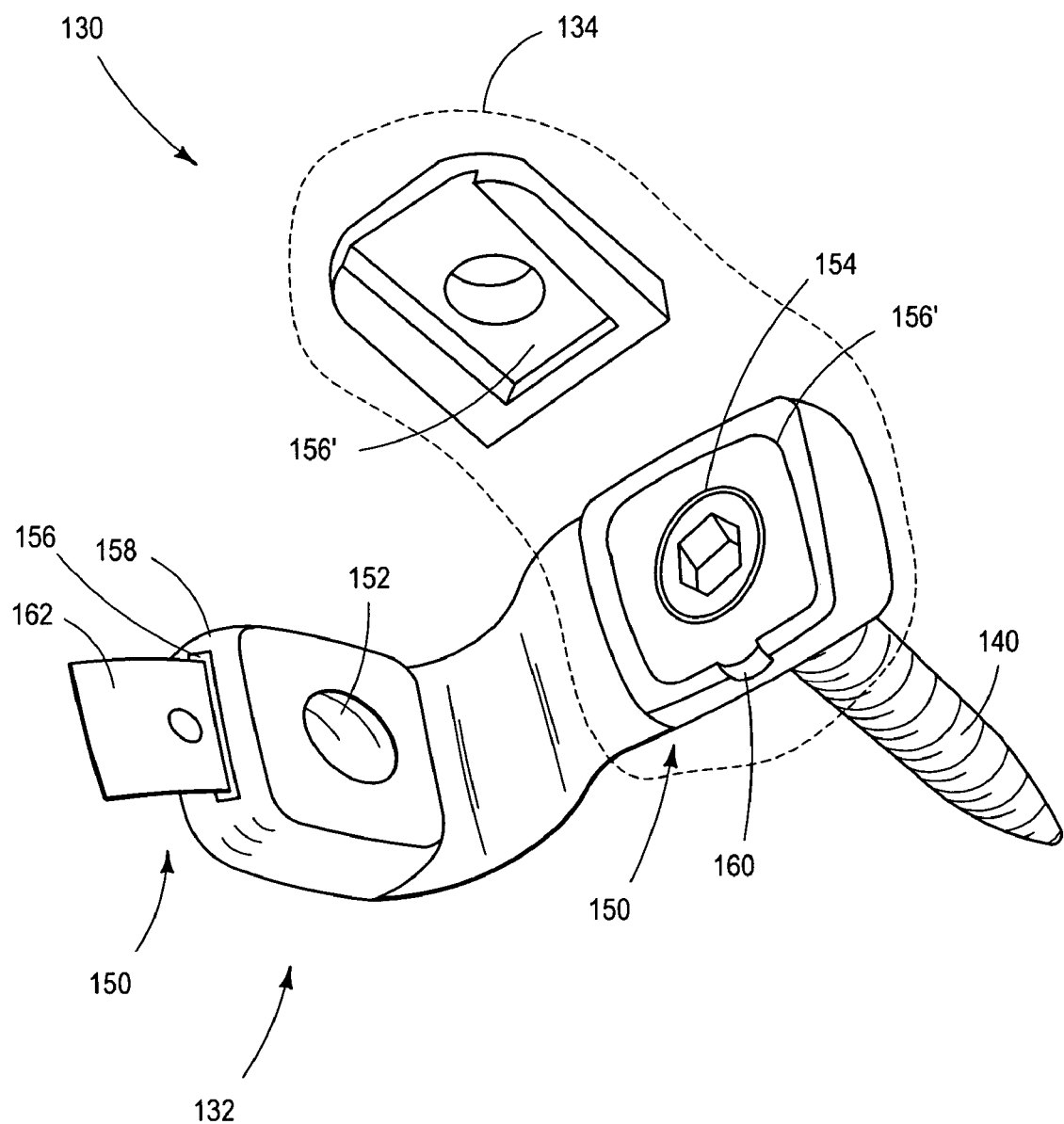
FIG. 12 is a perspective view of two anti-backout locking mechanisms that are integrated within a SLAF, in accord with one embodiment.
Figure 17:
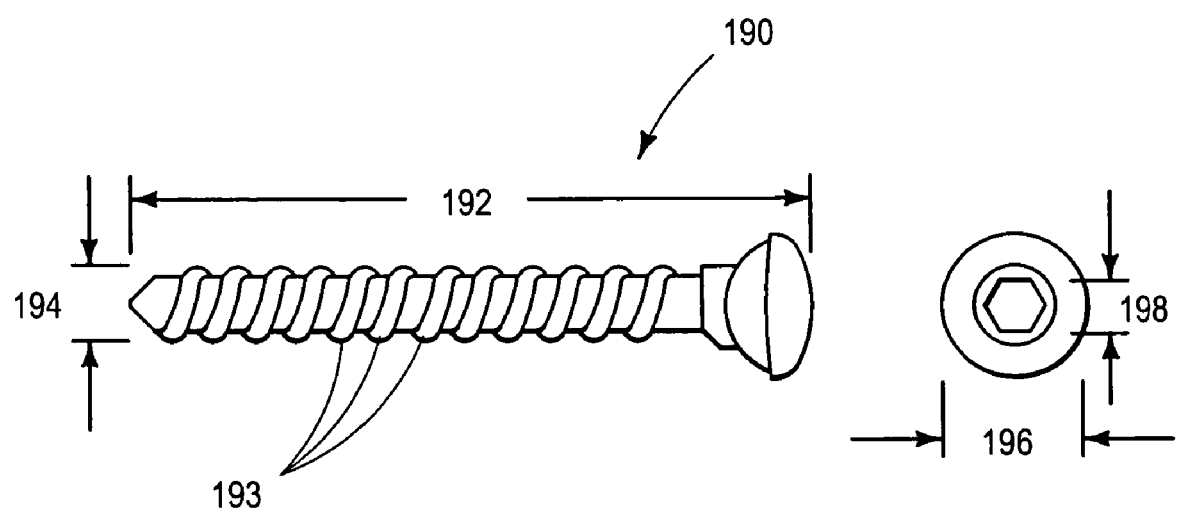
FIG. 17 shows one anti-backout 3.5 mm cancellous screw.

FIG. 12 is a perspective view of two anti-backout locking (ABL) mechanisms 150 that are integrated within SLAF 130, to prevent bone screws 140 and machine screws 128 from loosening or backing out of the femur 10 or non-shear bars 36 respectively, in accord with one embodiment. In northerly end 132 of SLAF 130, a hole 152 receives a machine screw 128 (not shown); in southerly end 134, a hole 154 receives a bone screw 140. In each ABL 150 is a hollow cavity or slot 156, 156' about 1.5 mm wide (also shown in FIG. 15) to receive an anti-backout tab 162. In northerly end 132, end face 158 of SLAF 130 has a slot 156, while in southerly end 134, side face 160 has a slot 156'. Southerly end 134 is shown split along slot 156' in FIG. 13 so that the internal structure of southerly end 134 may be viewed. Each of slots 156, 156' also includes a recess 160 for use with a stylus tool (as shown in FIG. 17).

Figure 13:
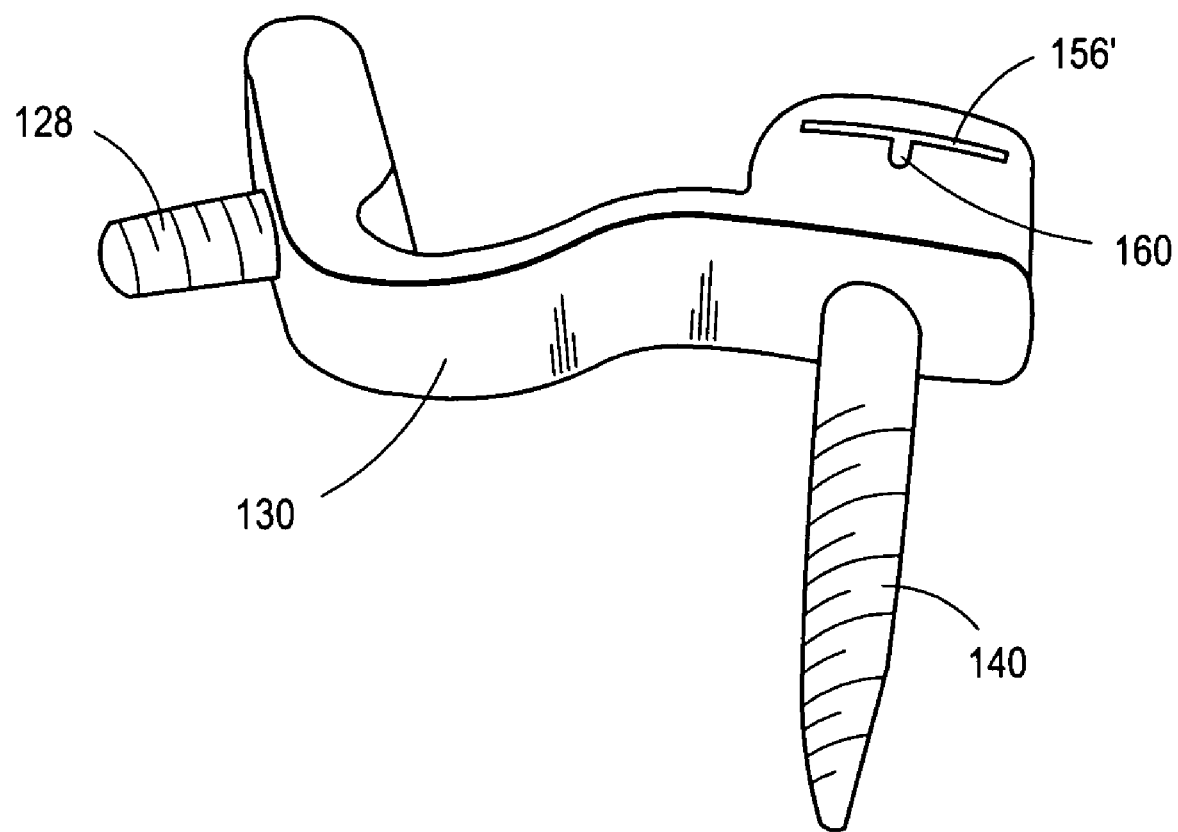
FIG. 13 is a side view of the SLAF of FIG. 12 showing a slot into which the anti-backout tab of FIG. 12 may be inserted to prevent back-out of a bone screw.

FIG. 13 is a side view of SLAF 130 showing slot 156' into which an anti-backout tab 162 may be inserted to prevent bone screw 140 from backing out. Recess 160, machine screw 128 and bone screw 140 are also shown.

Figure 14A:
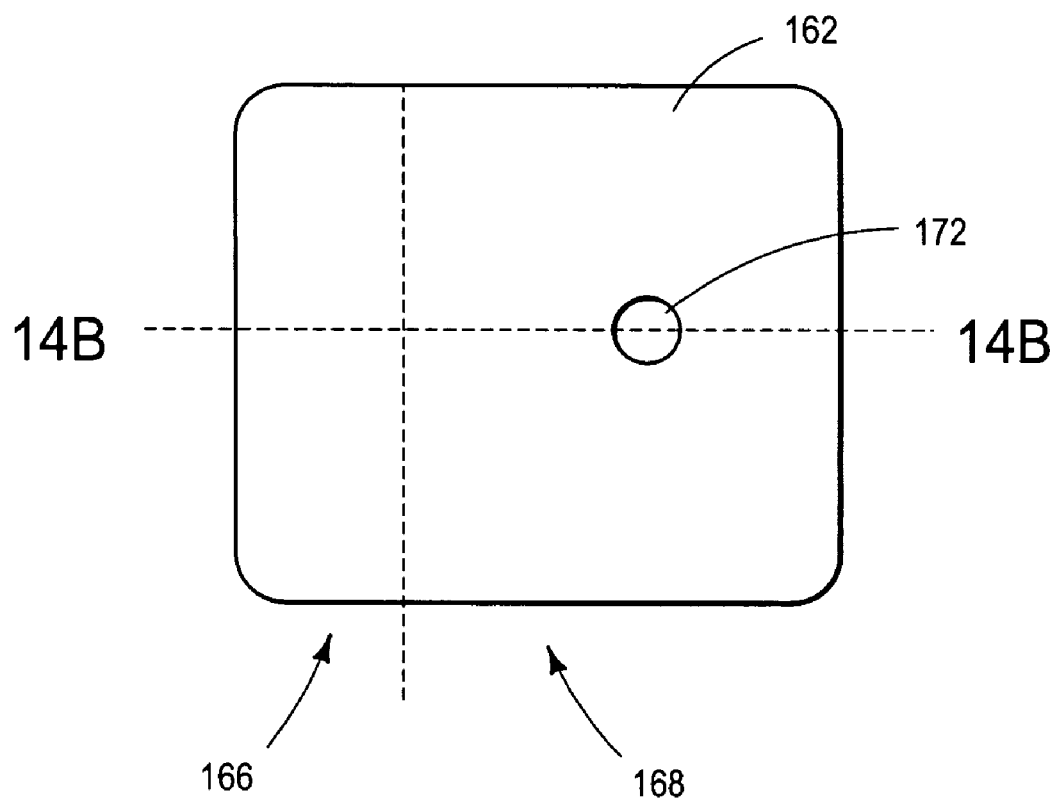
FIGS. 14A and 14B are top and side views of the anti-backout tab of FIG. 12.
Figure 14B:
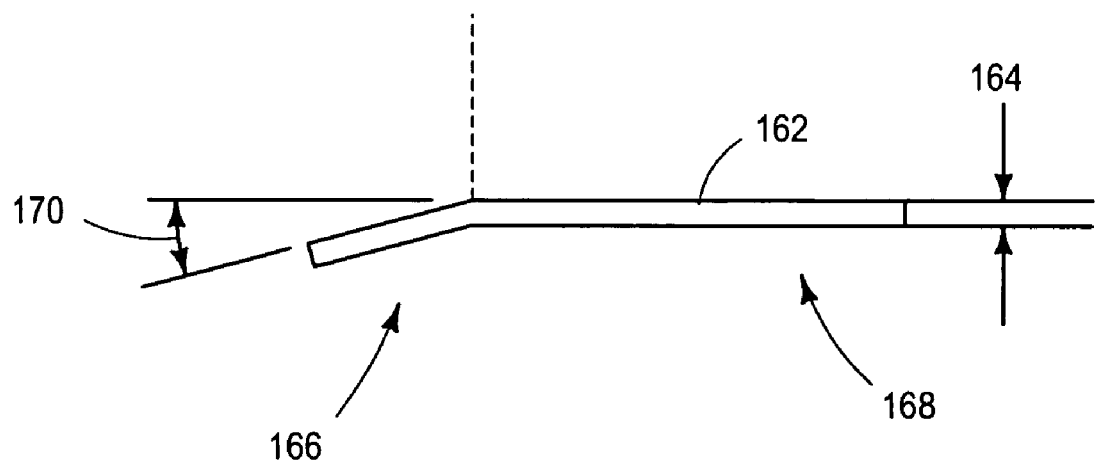

FIGS. 14A and 14B are top and side views of anti-backout tab 162, which has a thickness 164 of about 1.4 mm and is made of stainless spring steel. A proximal end 166 of anti-backout tab 162 has a downward bend 170 of approximately 10 degrees relative to a distal end 168, as shown. Anti-backout tab 162 also has a hole 172, as shown.

When inserted into slot 156, anti-backout tab 162 first straightens, then snaps back to its original bent shape when proximal end 166 moves past a lip 182 (see FIG. 16), thus locking the respective machine screw 128 or bone screw 140 in place. SLAF 130 may be made of stainless spring steel and be configured so that when northerly end 132 is attached to a non-shear fixator bar 36 by a machine screw 128, southerly end 134 is elevated by 3–4 mm (distance 136 shown in FIG. 11) off of the lower end of the femoral head 20. In this manner, when screwed down with bone screw 140, SLAF 130 delivers a southerly fixation force to cap 14.

Figure 15A:
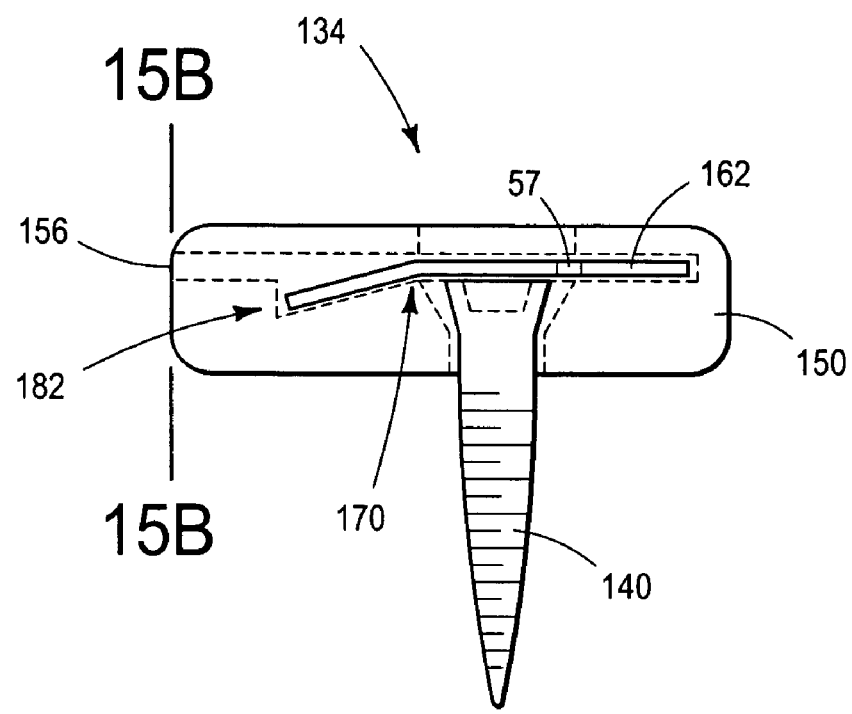
FIGS. 15A and 15B are enlarged side and end views of a southerly end of the SLAF of FIG. 12.
Figure 15B:
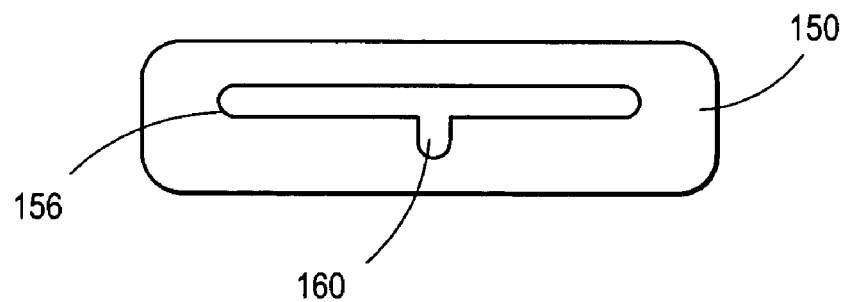

FIG. 15 is an enlarged side and end view of southerly end 134 of SLAF 130. Inside slot 156 is a lip 182 adapted to hold anti-backout tab 162. When fully inserted into slot 156 past lip 182, bend 170 snaps proximal end 166 of anti-backout tab 162 down so that anti-backout tab 162 does not work free of ABL 150, thus preventing bone screw 140 from backing out.

Figure 16:
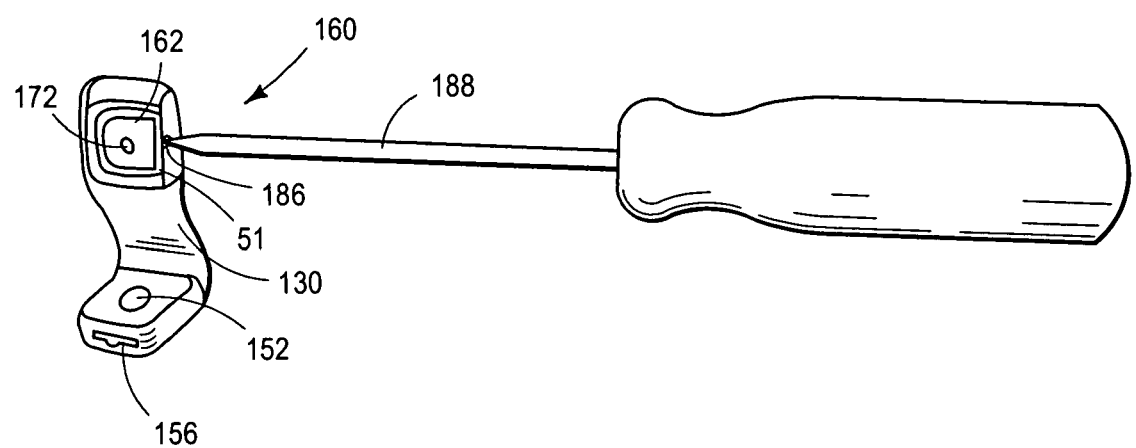
FIG. 16 shows how an anti-backout tab may be removed by a surgeon, to remove a bone screw.

FIG. 16 shows how anti-backout tab 162 may be removed by a surgeon for removal of a bone screw 140. A point 186 of a stylus 188 is inserted into groove 160 at the bottom of slot 156' of anti-backout tab 162 (also see FIGS. 9, 13 and 15). Groove 160 is deep enough to allow point 186 of stylus to get underneath anti-backout tab 162, so that pressure may be applied to straighten bend 170, enabling anti-backout tab 162 to move past lip 182. At the same time, a second stylus (not shown) may be inserted into hole 172 in anti-backout tab 162, to push anti-backout tab 162 out through slot 156', enabling removal of bone screw 140. An identical procedure may be used on a northerly end 132 of SLAF 130 to remove a machine screw 128.

FIG. 17 shows one anti-backout 3.5 mm cancellous screw 190. Screw 190 has a length 192 and threads 193, as shown. Exemplary dimensions of screw 190 may include a thread width 194 of 3.5 mm, a head diameter 196 of 6.0 mm, and a hex socket of 2.5 mm. Threads 193 have three notches (not shown), each notch about 0.025 mm deep and 0.03 mm wide, running lengthwise down about 70% of length 192, and each notch spaced an equal distance from adjacent notches about the circumference of screw 190. Once cancellous screw 190 is in place, bone growth can invade these notches, thus locking screw 190 in place, providing anti-backout capability.

Figure 18A:
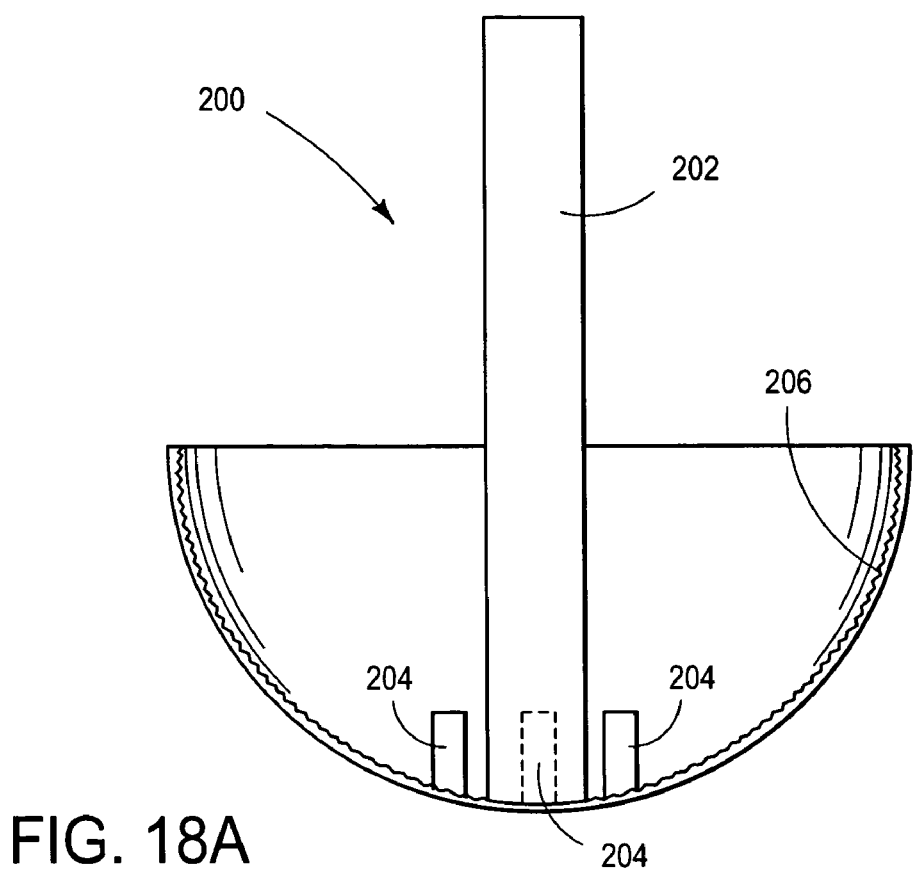
FIGS. 18A and 18B are a side cross-sectional view and a top view, respectively, of one femoral head resurfacing cap embodiment.
Figure 18B:
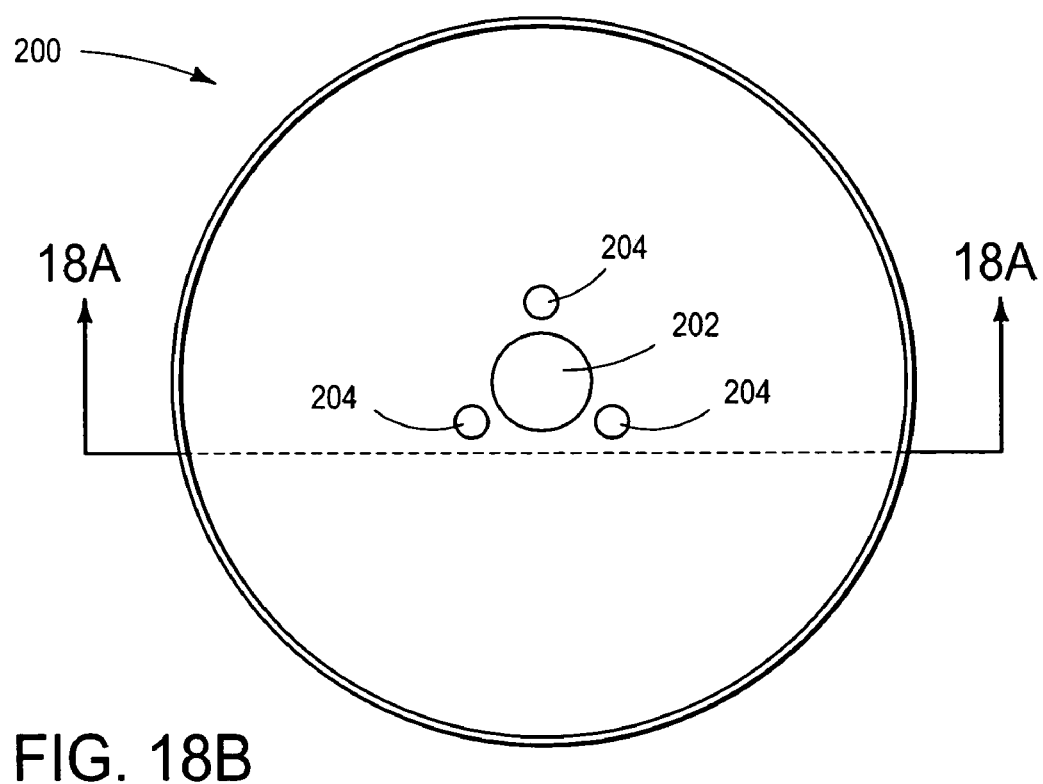

FIGS. 18A and 18B are a side cross-sectional view and a top view, respectively, of another femoral head resurfacing cap 200. Side cross-sectional view FIG. 18A is taken through a plane indicated by dashed line 18A—18A in FIG. 18B. A centering post 202 and one or more rods 204 are affixed to an inner surface 206 of shell 200. Rods 204 form stabilizing structure that may be inserted into corresponding holes or slots in a femoral head 20 (not shown) to stop migration or loosening of the shell in an equatorial or lateral direction. Once seated, shell 200 does not rotate equatorially without shearing femoral head 20. Additionally, rods 204 provide resistance to migration. Inner surface 206 of shell 200 may be coated with very small protuberances and indentations, such as a surface formed with hydroxyapatite porocast, to accept bone ingrowth and help fix cap 200 to femoral head 20.

Figure 19:
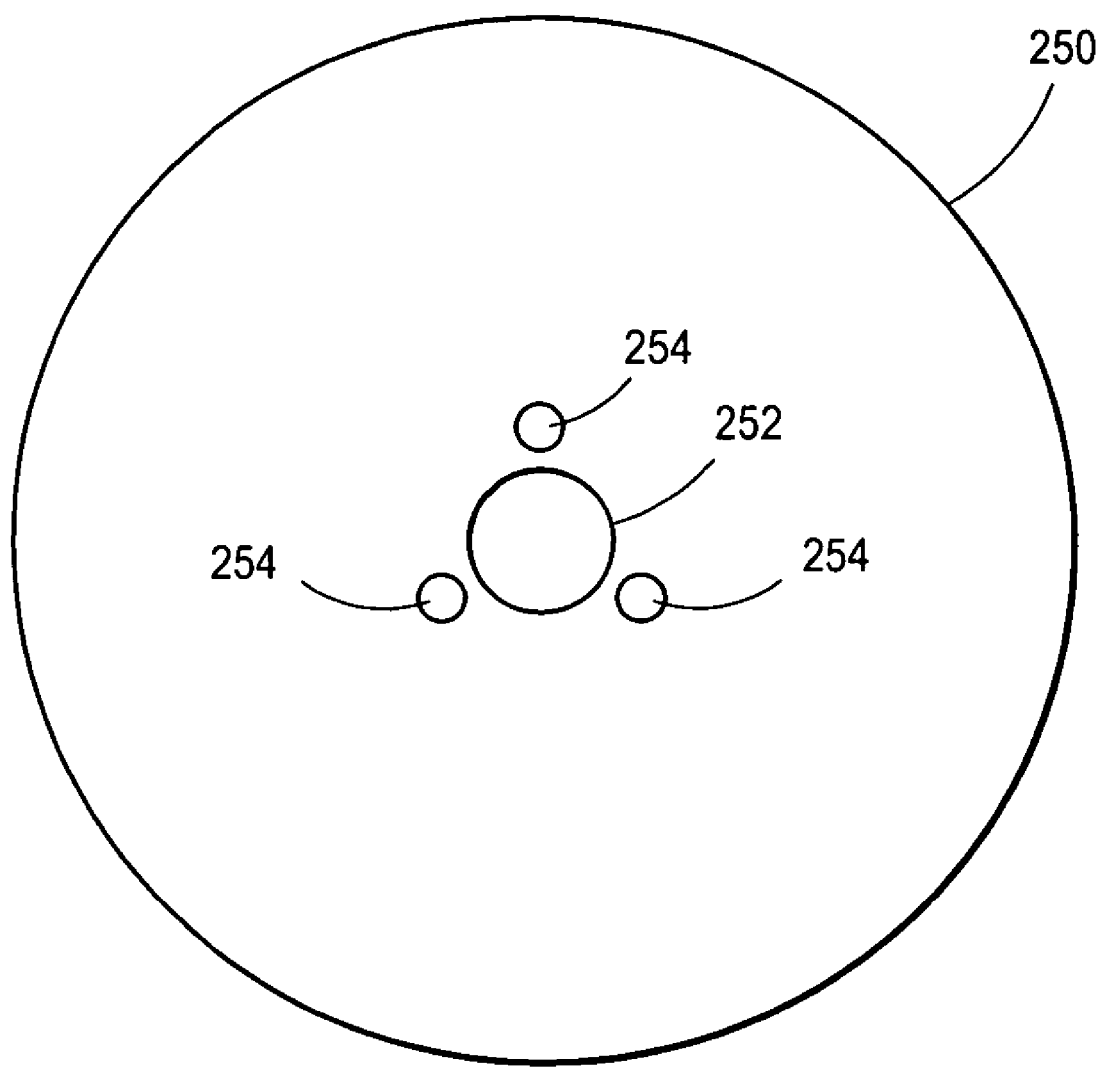
FIG. 19 shows a template for a central hole and side holes that may be made in a femoral head to accommodate the femoral head resurfacing cap of FIGS. 18A and 18B.

FIG. 19 shows a template 250 for a central hole 252 and side holes 254 that may be made in femoral head 20 (not shown) to accommodate femoral head resurfacing cap 200. Central hole 252 may be sized to match a diameter of centering post 202 of cap 200, and side holes 254 may be sized to match a diameter of rods 204. A surgeon may use template 250 to mark sites on a femoral head for drilling, or may drill holes with template 250 in place.

Although FIGS. 18A, 18B and 19 show stabilizing structure of three rods 204, and a template 250 for holes to accommodate three rods 204, a different number or type of structure may be used. For example, more or fewer rods 204 may be used. Furthermore, a stabilizing structure may be of another shape, for example, it may include members that are round, square, or triangular. A stabilizing structure may abut centering post 202, or may be affixed to inner surface 206 at locations which are not adjacent to the centering post. Alternatively, a stabilizing structure may be formed monolithically with centering post 202; for example, rods 204 may be fins or fin-like dowels extending from centering post 202. A template (i.e., like template 250) may be configured to locate sites for cutting holes, slots or other openings in a femoral head to accommodate the number, locations, and shapes of rods 204.

Figure 20A:
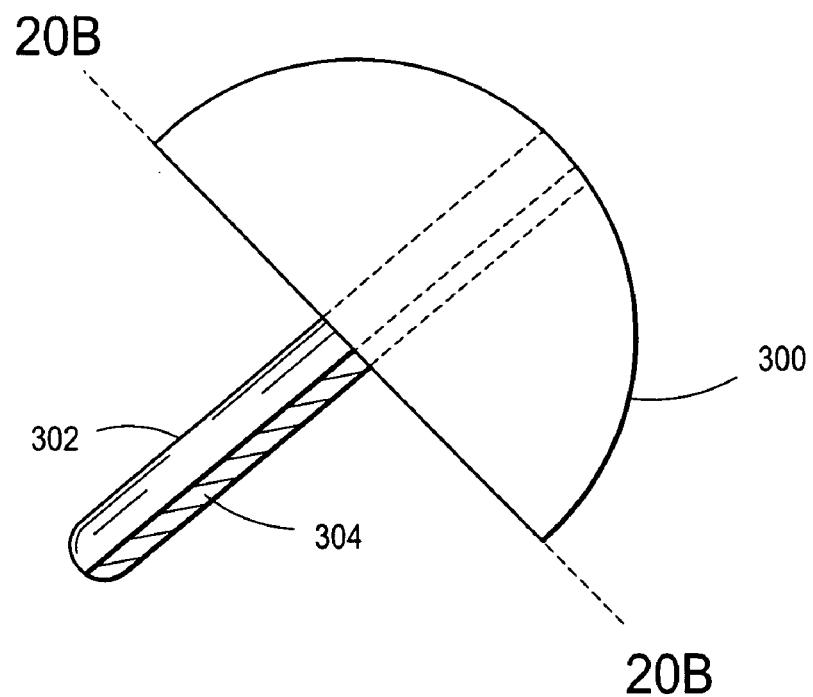
FIGS. 20A and 20B show, respectively, a perspective view and an end view of a femoral head cap that has a stem with a lengthwise groove.
Figure 20B:
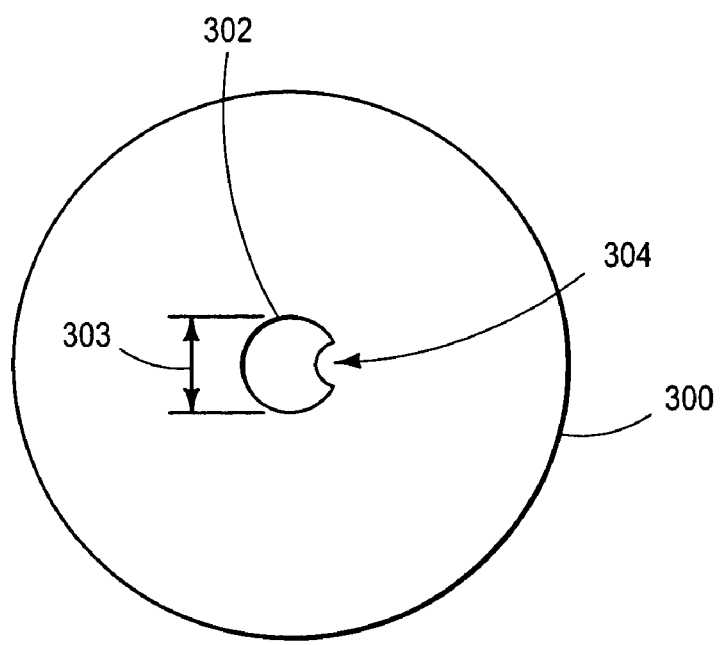

FIGS. 20A and 20B show, respectively, a perspective view and an end view of a femoral head cap 300 that has a stem 302 with a lengthwise groove 304. Stem 302 may be approximately 3 to 4 centimeters long, and may be circular in cross-section with a diameter 303, except at groove 304. Groove 304 is a semi-circular recess within stem 302.

Figure 20C:
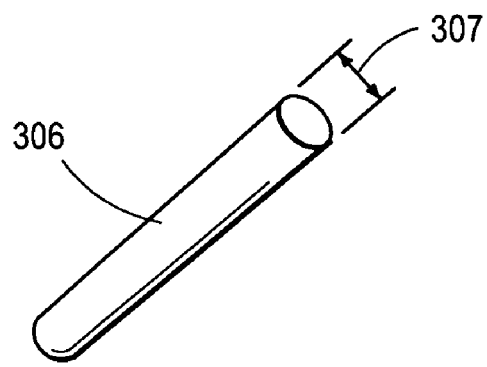
FIGS. 20C and 20D show, respectively, a dowel for use with the femoral head cap of FIGS. 20A and 20B, and an end view of the femoral head cap of FIGS. 20A and 20B with the dowel.
Figure 20D:
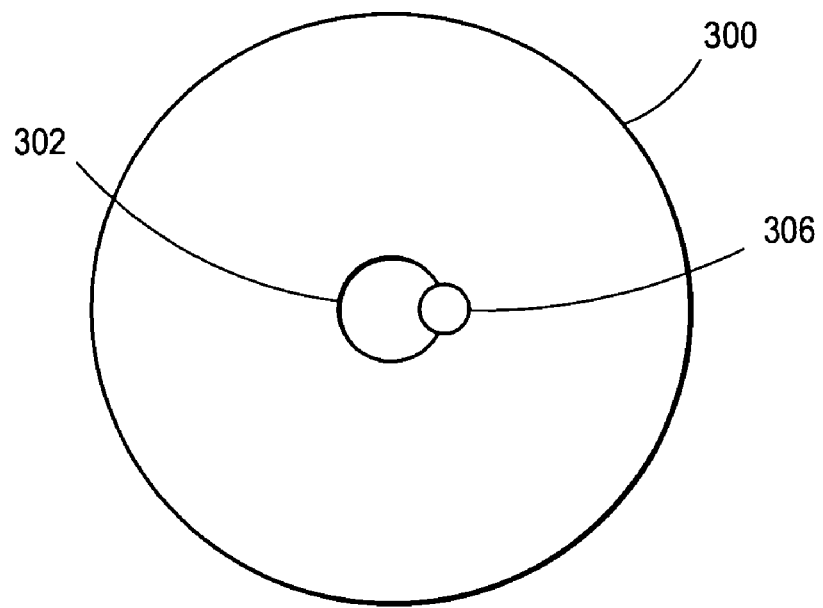

FIGS. 20C and 20D show, respectively, a dowel 306 for use with femoral head cap 300 and an end view of femoral head cap 300 with dowel 306. Dowel 306 is shorter than stem 302, and is adapted to fit snugly into groove 304, as shown, to form a stabilizing structure. A diameter 307 of dowel 306 may be, for example, 10% to 50% of diameter 303 of stem 302.

Although FIGS. 20A, 20B and 20D show stabilizing structure of one dowel 306, and a femoral head 310 with a hole to accommodate dowel 306, more than one dowel 306 may be used, with additional stem grooves (i.e., like groove 304) and femoral head holes (i.e., like hole 314) to accommodate each dowel 306. Multiple dowels 306 may be identically sized, or may be different from one another, with corresponding adjustments to the stem grooves and femoral head holes.

Figure 21A:
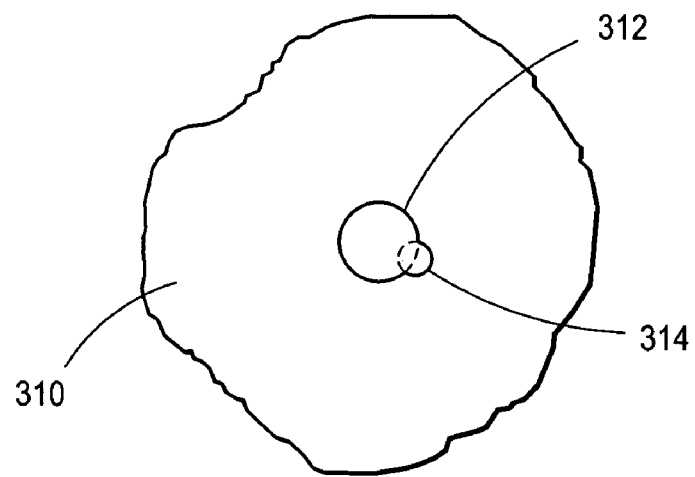
FIGS. 21A and 21B show an end view and a side view, respectively, of a femoral head with holes drilled to accept the stem of FIGS. 20A, 20B and 20D and the dowel of FIGS. 20C and 20D.
Figure 21B:
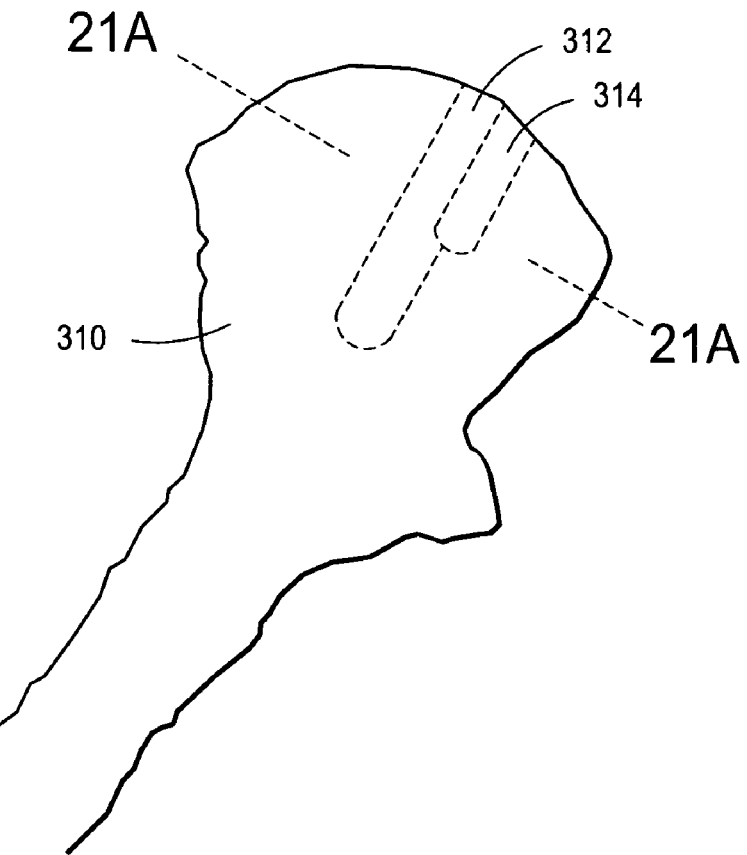

FIGS. 21A and 21B show an end view and a side view, respectively, of a femoral head 310 with holes 312, 314 drilled to accept stem 302 and dowel 306. Hole 312 has a sufficient diameter and depth to accept stem 302, and hole 314 has a sufficient depth and diameter to accept stem 304. To install femoral head cap 300, a surgeon (optionally using a template with appropriately located and sized holes) drills holes 312 and 314. The surgeon then inserts dowel 306 into groove 304, and slides stem 302 and dowel 306 into holes 312 and 314, respectively. Hole 314 holds dowel 306 in place, and dowel 306 in turn prevents stem 302 and cap 300 from rotating with respect to femoral head 310. Hole 312 holds stem 302 in place and prevents cap 300 from migrating.

The changes described above, and others, may be made in the femoral head resurfacing apparatus and methods described herein without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. Femoral head resurfacing apparatus, comprising
   (a) a cap having a substantially hemispherical shape of substantially uniform thickness; and
   (b) a plurality of non-shear fixation bars, the non-shear fixation bars comprising a plurality of gear shaped teeth to encourage bone ingrowth between the teeth, an equatorial end of each non-shear fixation bar forming a hole configured to accept a screw for attaching mounting hardware to couple the cap with the femoral head.

2. Apparatus of claim 1, an inner surface of the cap and the sides of the non-shear bars comprising hydroxyapatite porocast to provide and promote bone ingrowth-penetration into the cap to facilitate additional fixation of the cap to the femoral head.

3. Apparatus of claim 1, the cap being sized to minimize bone removal from the femoral head.

4. Apparatus of claim 1, further comprising the mounting hardware, the mounting hardware comprising one or more spring loaded absorption fixators, each fixator attaching to one of the non-shear fixation bars using the screw.

5. Apparatus of claim 1, further comprising a plurality of bone screws each having threads notched in equidistant spots from the screw head down about 70% of the length of each screw.

6. Femoral head resurfacing apparatus, comprising
   (a) a cap having a substantially hemispherical shape of substantially uniform thickness, the cap configured to interface with a metal cup socket maintaining a clearance tolerance of 0.01 mm; and
   (b) a plurality of non-shear fixation bars for insertion into respective longitudinal slots cut into the femoral head, an equatorial end of each non-shear fixation bar forming a hole configured to accept a screw for attaching mounting hardware to couple the cap with the femoral head.

7. Femoral head resurfacing apparatus, comprising
   (a) a cap having a substantially hemispherical shape of substantially uniform thickness; the cap being fixed by a plurality of metal spring loaded absorption fixators, each fixator being screwed into the cap and femoral head, to prevent loosening of the cap and
   (b) a plurality of non-shear fixation bars for insertion into respective longitudinal slots cut into the femoral head, wherein the cap remains substantially immovable other than due northerly.

8. Apparatus of claim 7, the spring loaded absorption fixators having ability to flex and absorb forces and stress similar to the way bone flexes.

9. Apparatus of claim 7, a southerly end of the spring loaded absorption fixators being compressed when screwed into the femoral head to deliver a force to the cap while fixed to the femoral head.

10. Apparatus of claim 7, the spring loaded absorption fixator comprising anti-back out locking means.

11. Apparatus of claim 10, the anti-back out locking means being removable by a surgeon by use of a pointed stylus instrument.

12. A method of resurfacing the femoral head of a hip joint, comprising the steps of:
    removing a plurality of longitudinal slots of bone in the femoral head; and
    attaching a hemispherical cap to the head, the cap forming a plurality of non-shear fixation bars for mating engagement with the slots.

13. The method of claim 12, wherein the step of attaching comprises utilizing a plurality of metal spring loaded absorption fixators, and further comprising screwing each of the fixators to the cap and to the femoral head.

14. A femoral head resurfacing cap, comprising:
    a hollow cap to mate with a plurality of longitudinal slots within a femoral head of the hip joint, the cap forming non-shear bars for mating engagement with the slots; and
    a plurality of spring-loaded absorption fixators for attaching the cap to the head.

15. The femoral head resurfacing cap of claim 14, further comprising a plurality of screws, each of the screws coupling one of the fixators to the cap and the head.

16. The femoral head resurfacing cap of claim 14, wherein the fixators comprise hydroxyapatite porocast to facilitate bone growth attachment to the fixators.

17. The femoral head resurfacing cap of claim 14, wherein the cap forms a hollow interior hemisphere surface to accommodate the head, the cap further comprising hydroxyapatite porocast to facilitate bone growth attachment to the cap.

18. A method for capping a femoral head with a shell, comprising the steps of:
    inserting a centering device in a centering hole of the femoral head;
    drilling a plurality of holes about the centering hole, a diameter of the holes being from between about 3 mm to 12 mm, a depth of the holes being about 6 mm; and
    inserting fin-like dowels, which are a part of a centering hole post, into the holes to prevent migration of the shell.

* * * * *